(12) United States Patent
Mukherjee et al.

(10) Patent No.: US 12,266,431 B2
(45) Date of Patent: Apr. 1, 2025

(54) MACHINE LEARNING ENGINE AND RULE ENGINE FOR DOCUMENT AUTO-POPULATION USING HISTORICAL AND CONTEXTUAL DATA

(71) Applicant: CERNER INNOVATION, INC., Kansas City, KS (US)

(72) Inventors: Tanmoy Mukherjee, Kolkata (IN); Shrilata Mondal, Guskara Bardhaman (IN); Debendra Kar, Marathalli Bangalore (IN); Damodar Reddy Karra, Telangana (IN)

(73) Assignee: Cerner Innovation, Inc., Kansas City, MO (US)

( * ) Notice: Subject to any disclaimer, the term of this patent is extended or adjusted under 35 U.S.C. 154(b) by 420 days.

(21) Appl. No.: 17/221,981

(22) Filed: Apr. 5, 2021

(65) Prior Publication Data
US 2022/0319646 A1   Oct. 6, 2022

(51) Int. Cl.
*G16H 10/60* (2018.01)
*G06F 40/174* (2020.01)
*G06F 40/20* (2020.01)

(52) U.S. Cl.
CPC .......... *G16H 10/60* (2018.01); *G06F 40/174* (2020.01); *G06F 40/20* (2020.01)

(58) Field of Classification Search
CPC ........ G16H 10/60; G16H 50/70; G16H 15/00; G06F 40/169; G06F 40/20; G06F 40/174; G06F 16/3344; G06F 16/35; G06F 16/906
USPC .......................................................... 705/2
See application file for complete search history.

(56) References Cited

U.S. PATENT DOCUMENTS

| 6,137,911 A | * | 10/2000 | Zhilyaev | G06F 16/353 |
| | | | | 382/229 |
| 7,379,946 B2 | | 5/2008 | Carus et al. | |
| 7,881,957 B1 | | 2/2011 | Cohen et al. | |
| 7,885,811 B2 | | 2/2011 | Zimmerman et al. | |
| 8,170,897 B1 | | 5/2012 | Cohen et al. | |

(Continued)

FOREIGN PATENT DOCUMENTS

WO   WO-2017205850 A1 * 11/2017 ............. G06N 20/00

OTHER PUBLICATIONS

Final Office Action received for U.S. Appl. No. 16/720,641, mailed on Jan. 11, 2022, 18 pages.

(Continued)

*Primary Examiner* — Karen A Hranek
*Assistant Examiner* — Teresa S Williams
(74) *Attorney, Agent, or Firm* — Invoke

(57) ABSTRACT

Methods, systems, and computer-readable media are disclosed herein for a machine learning engine and rule engine that leverage historical and contextual data to intelligently identify, score, and suggest one or more documents for auto-population of a graphical user interface. The machine learning and rule engine employ vectorization and clustering technique to identify, score, and suggest the most factually accurate and contextually relevant documents as selectable candidates for electronic documentation. Further, the selection, rejection, or modification of the candidate documents are ingested by the machine learning engine and/or the rule engine to update a clustering algorithm and/or to update a relevance scoring algorithm, which are then utilized for subsequent instances.

40 Claims, 16 Drawing Sheets

(56) References Cited

U.S. PATENT DOCUMENTS

| | | |
|---|---|---|
| 8,185,553 B2 | 5/2012 | Carus et al. |
| 8,209,183 B1 | 6/2012 | Patel et al. |
| 8,255,258 B1 | 8/2012 | Cohen et al. |
| 8,374,865 B1 | 2/2013 | Biadsy et al. |
| 8,428,940 B2 | 4/2013 | Kristjansson et al. |
| 8,498,892 B1 | 7/2013 | Cohen et al. |
| 8,510,340 B2 | 8/2013 | Carus et al. |
| 8,612,211 B1 | 12/2013 | Shires et al. |
| 8,694,335 B2 | 4/2014 | Yegnanarayanan |
| 8,700,395 B2 | 4/2014 | Zimmerman et al. |
| 8,738,403 B2 | 5/2014 | Flanagan et al. |
| 8,756,079 B2 | 6/2014 | Yegnanarayanan |
| 8,768,723 B2 | 7/2014 | Montyne et al. |
| 8,782,088 B2 | 7/2014 | Carus et al. |
| 8,788,289 B2 | 7/2014 | Flanagan et al. |
| 8,799,021 B2 | 8/2014 | Flanagan et al. |
| 8,831,957 B2 | 9/2014 | Taubman et al. |
| 8,878,773 B1 | 11/2014 | Bozarth |
| 8,880,406 B2 | 11/2014 | Santos-lang et al. |
| 8,924,211 B2 | 12/2014 | Ganong et al. |
| 8,953,886 B2 | 2/2015 | King et al. |
| 8,972,243 B1 | 3/2015 | Strom et al. |
| 8,977,555 B2 | 3/2015 | Torok et al. |
| 9,058,805 B2 | 6/2015 | Aleksic et al. |
| 9,117,451 B2 | 8/2015 | Fructuoso et al. |
| 9,129,013 B2 | 9/2015 | Delaney et al. |
| 9,135,571 B2 | 9/2015 | Delaney et al. |
| 9,147,054 B1 | 9/2015 | Beal et al. |
| 9,152,763 B2 | 10/2015 | Carus et al. |
| 9,240,187 B2 | 1/2016 | Torok et al. |
| 9,257,120 B1 | 2/2016 | Alvarez Guevara et al. |
| 9,269,012 B2 | 2/2016 | Fotland |
| 9,292,089 B1 | 3/2016 | Sadek |
| 9,304,736 B1 | 4/2016 | Whiteley et al. |
| 9,318,104 B1 | 4/2016 | Fructuoso et al. |
| 9,324,323 B1 | 4/2016 | Bikel et al. |
| 9,343,062 B2 | 5/2016 | Ganong et al. |
| 9,378,734 B2 | 6/2016 | Ganong et al. |
| 9,384,735 B2 | 7/2016 | White et al. |
| 9,420,227 B1 | 8/2016 | Shires et al. |
| 9,424,840 B1 | 8/2016 | Hart et al. |
| 9,443,509 B2 | 9/2016 | Ganong et al. |
| 9,466,294 B1 | 10/2016 | Tunstall-pedoe et al. |
| 9,538,005 B1 | 1/2017 | Nguyen et al. |
| 9,542,944 B2 | 1/2017 | Jablokov et al. |
| 9,542,947 B2 | 1/2017 | Schuster et al. |
| 9,552,816 B2 | 1/2017 | Vanlund et al. |
| 9,563,955 B1 | 2/2017 | Kamarshi et al. |
| 9,569,594 B2 | 2/2017 | Casella Dos Santos |
| 9,570,076 B2 | 2/2017 | Sierawski et al. |
| 9,601,115 B2 | 3/2017 | Chen et al. |
| 9,678,954 B1 | 6/2017 | Cuthbert et al. |
| 9,679,107 B2 | 6/2017 | Cardoza et al. |
| 9,721,570 B1 | 8/2017 | Beal et al. |
| 9,786,281 B1 | 10/2017 | Adams et al. |
| 9,792,914 B2 | 10/2017 | Alvarez Guevara et al. |
| 9,805,315 B1 | 10/2017 | Cohen et al. |
| 9,898,580 B2 | 2/2018 | Flanagan et al. |
| 9,904,768 B2 | 2/2018 | Yegnanarayanan |
| 9,911,418 B2 | 3/2018 | Chi |
| 9,916,420 B2 | 3/2018 | Cardoza et al. |
| 9,922,385 B2 | 3/2018 | Yegnanarayanan |
| 9,971,848 B2 | 5/2018 | D'souza et al. |
| 10,032,127 B2 | 7/2018 | Habboush et al. |
| 10,347,117 B1 | 7/2019 | Capurro |
| 10,602,974 B1 | 3/2020 | Govindjee et al. |
| 10,951,762 B1 | 3/2021 | Brandt et al. |
| 11,024,424 B2* | 6/2021 | Sun .................. G16H 10/60 |
| 2008/0177537 A1 | 7/2008 | Ash et al. |
| 2009/0100358 A1 | 4/2009 | Lauridsen et al. |
| 2009/0138288 A1 | 5/2009 | Benja-athon |
| 2009/0268882 A1 | 10/2009 | Lee et al. |
| 2010/0161353 A1 | 6/2010 | Mayaud |
| 2011/0178931 A1 | 7/2011 | Kia |
| 2012/0066197 A1* | 3/2012 | Rana ............... G06F 16/24578 |
| | | 707/706 |
| 2014/0350961 A1 | 11/2014 | Csurka et al. |
| 2015/0006199 A1 | 1/2015 | Snider et al. |
| 2015/0142418 A1 | 5/2015 | Byron et al. |
| 2015/0169827 A1 | 6/2015 | Laborde |
| 2015/0340033 A1 | 11/2015 | Di Fabbrizio et al. |
| 2016/0119305 A1 | 4/2016 | Panchura et al. |
| 2017/0116373 A1 | 4/2017 | Ginsburg et al. |
| 2018/0012604 A1 | 1/2018 | Guevara et al. |
| 2018/0113676 A1* | 4/2018 | De Sousa Webber .... G06F 7/20 |
| 2018/0166076 A1 | 6/2018 | Higuchi et al. |
| 2018/0308490 A1 | 10/2018 | Lim et al. |
| 2018/0322110 A1 | 11/2018 | Rhodes et al. |
| 2018/0373844 A1 | 12/2018 | Ferrandez-escamez et al. |
| 2019/0121532 A1 | 4/2019 | Strader et al. |
| 2019/0130073 A1 | 5/2019 | Sun et al. |
| 2019/0206524 A1 | 7/2019 | Baldwin et al. |
| 2019/0272919 A1 | 9/2019 | Frandsen et al. |
| 2019/0287665 A1 | 9/2019 | Forsberg et al. |
| 2019/0311807 A1 | 10/2019 | Kannan et al. |
| 2019/0362846 A1* | 11/2019 | Vodencarevic ......... G16H 50/20 |
| 2020/0034366 A1* | 1/2020 | Kivatinos ............. G06F 16/285 |
| 2022/0335942 A1 | 10/2022 | Agassi et al. |
| 2022/0344049 A1* | 10/2022 | Hall ..................... G06N 3/0464 |

OTHER PUBLICATIONS

Pre-Interview First Office action received for U.S. Appl. No. 16/720,632, mailed on Feb. 17, 2022, 4 pages.

Pre interview First Office Action received for U.S. Appl. No. 16/720,644, mailed on Aug. 4, 2022, 4 pages.

Chiu et al., "Speech Recognition for Medical Conversations", Available Online at: <arXiv preprint arXiv:1711.07274>, Nov. 20, 2017, 5 pages.

Final Office Action received for U.S. Appl. No. 16/720,632, mailed on Oct. 19, 2022, 31 pages.

Non-Final Office Action received for U.S. Appl. No. 17/132,859, mailed on Nov. 22, 2022, 30 pages.

Preinterview First Office Action of U.S. Appl. No. 16/720,641, mailed on Oct. 14, 2021, 7 pages.

* cited by examiner

200

CONT. FROM 2A

↓

216
IDENTIFY A PRIMARY CLUSTER IN THE PLURALITY OF CLUSTERS THAT IS A BEST MATCH TO THE COMBINED VECTOR

↓

218
PERFORM NATURAL LANGUAGE PROCESSING OF A PLURALITY OF TEXT BLOCKS THE PRIMARY CLUSTER

↓

220
ASSIGN A RELEVANCE SCORE FOR EACH OF THE PLURALITY OF TEXT BLOCKS IN THE PRIMARY CLUSTER

↓

222
IDENTIFY A PRIMARY TEXT BLOCK IN THE PLURALITY OF TEXT BLOCKS OF THE PRIMARY CLUSTER HAVING A HIGHEST RELEVANCE SCORE

↓

224
COMMUNICATE THE PRIMARY TEXT BLOCK FOR DISPLAY AS A RECOMMENDED SELECTION FOR AUTOMATIC POPULATION OF AN ELECTRONIC DOCUMENT

*FIG. 2B.*

| Age | Gender | Weight | | Problems | Diagnosis | Allergies |
|-----|--------|--------|---|----------|-----------|-----------|
| A1 | M | W1 | * | 234789008 | B78.121F | AL1 |
| A2 | F | W2 | * | 67899009 | | AL3 |
| A2 | F | W2 | * | 567800089 | A34.988E | X |
| A3 | F | W3 | * | 234789008 | C76.987B | AL5 |
| * | * | * | * | * | * | * |
| * | * | * | * | * | B78.121F | * |

FIG. 3.

| Age | Weight | 234789008 | 67899009 | 567800089 | B78.121F | A34.988E | C76.987B | AL1 | AL3 | AL5 | Note Data |
|---|---|---|---|---|---|---|---|---|---|---|---|
| A1 | W1 | 1 | 1 | 0 | 1 | 0 | 0 | 1 | 1 | 0 | ND1 |
| A2 | W2 | 0 | 0 | 1 | 0 | 1 | 0 | 0 | 0 | 0 | ND2 |
| A3 | W3 | 1 | 0 | 0 | 1 | 0 | 1 | 0 | 0 | 1 | ND3 |
| * | * | * | * | * | * | * | * | * | * | * | * |

| Age | Weight | 234789008 | 67899009 | 5678000089 | B78.121F | A34.988E | C76.987B | AL1 | AL3 | AL5 | Note Data | Cluster |
|---|---|---|---|---|---|---|---|---|---|---|---|---|
| A1 | W1 | 1 | 1 | 0 | 1 | 0 | 0 | 1 | 1 | 0 | ND1 | C1 |
| A2 | W2 | 0 | 0 | 1 | 0 | 1 | 0 | 0 | 0 | 0 | ND2 | C3 |
| A3 | W3 | 1 | 0 | 0 | 1 | 0 | 1 | 0 | 0 | 1 | ND3 | C1 |
| * | * | * | * | * | * | * | * | * | * | * | * | * |

FIG. 5.

Chief Complaint

My stomach hurts and I feel full of gas.

History of Present Illness

47 year old male with mid-abdominal epigastric pain, associated with severe nausea & vomiting; unable to keep down any food or liquid. Pain has become "severe" and constant.
Has had an estimated 13 pound weight loss over the past month.
Patient reports eating 12 sausages at the Sunday church breakfast five days ago which he believes initiated his symptoms.
Patient admits to a history of alcohol dependence. Consuming 5 – 6 beers per day now, down from 10 – 12 per day 6 months ago. States that he has nausea and sweating with "the shakes" when he does not drink.
Allergy to penicillin.

Assessment and Plan

*FIG. 7.*

| Age | Weight | R10.9 | 67899009 | 567800089 | B78.121F | K29.20 | C76.987B | R11.2 | F10.229 | F10.29 | Z88.10 | Z88.0 | * |
|---|---|---|---|---|---|---|---|---|---|---|---|---|---|
| 47 | 146 | 1 | 0 | 0 | 0 | 1 | 0 | 1 | 0 | 1 | 1 | 0 | * |

FIG. 8.

Block 1:
Crohn's disease, large intestine with abscess [K50.114]. Awaiting GI consultation. Old myocardial infarction [I25.2]. Allergy to antibiotic agent [Z88.1]. Allergy to penicillin Zz88.0. Personal history of nicotine dependence or personal history of tobacco use [Z87.891].

Block 2:
Dehydration and suspected acute pancreatitis [K85] with abdominal pain [R10.9]. Admit to the hospital if abdominal pain [R10.9] does not reduce. Orders written and sent to on-call hospitalist. 1L IV NS started in office. Blood drawn for labs. Recommend behavioral health counseling for alcohol abuse assessment and possible treatment [F10.29]. Patient's wife notified of plan; she will transport to hospital by private vehicle. Allergy to peanuts [Z88.10].

*FIG. 9.*

Term array (T) = [R10.9, K29.20, R11.2, F10.29, Z88.0]

Document array (D) = ["Crohn's disease, large intestine with abscess [K50.114] with abdominal pain [R10.9]. Awaiting GI consultation. Old myocardial infarction [I25.2]. Allergy to antibiotic agent [Z88.1]. Personal history of nicotine dependence or personal history of tobacco use [Z87.891].", "Dehydration and suspected acute pancreatitis [K85] with abdominal pain [R10.9]. Admit to the hospital if abdominal pain [R10.9] does not reduce. Orders written and sent to on-call hospitalist. 1L IV NS started in office. Blood drawn for labs. Recommend behavioral health counseling for alcohol abuse assessment and possible treatment [F10.29]. Patient's wife notified of plan; she will transport to hospital by private vehicle. Allergy to penicillin [Z88.0]. Allergy to peanuts [Z88.10]."]

*FIG. 10.*

For D = 2,

T = 1: 2/6*log2/1 * 2/4 = 0.0501
Calculating similarly, we get,
T = 2: 0
T = 3: 0
T = 4: 0.0125
T = 5: 0.0125
Document_relevance_score = 0.0751

Chief Complaint

My stomach hurts and I feel full of gas.

History of Present Illness

47 year old male with mid-abdominal epigastric pain, associated with severe nausea & vomiting; unable to keep down any food or liquid.
Pain has become "severe" and constant.
Has had an estimated 13 pound weight loss over the past month.
Patient reports eating 12 sausages at the Sunday church breakfast five days ago which he believes initiated his symptoms.
Patient admits to a history of alcohol dependence. Consuming 5 – 6 beers per day now, down from 10 – 12 per day 6 months ago. States that he has nausea and sweating with "the shakes" when he does not drink.
Allergy to penicillin.

Assessment and Plan

Dehydration and suspected acute pancreatitis with abdominal pain. Admit to the hospital if abdominal pain does not reduce. Orders written and sent to on-call hospitalist. 1L IV NS started in office. Blood drawn for labs. Recommend behavioral health counseling for alcohol abuse assessment and possible treatment. Patient's wife notified of plan, she will transport to hospital by private vehicle. Allergy to penicillin. Allergy to peanuts.

Chief Complaint

My stomach hurts and I feel full of gas.

History of Present Illness

47 year old male with mid-abdominal epigastric pain, associated with severe nausea & vomiting; unable to keep down any food or liquid. Pain has become "severe" and constant.
Has had an estimated 13 pound weight loss over the past month.
Patient reports eating 12 sausages at the Sunday church breakfast five days ago which he believes initiated his symptoms.
Patient admits to a history of alcohol dependence. Consuming 5 – 6 beers per day now, down from 10 – 12 per day 6 months ago. States that he has nausea and sweating with "the shakes" when he does not drink.
Allergy to penicillin.

Assessment and Plan

Crohn's disease, large intestine with abscess with abdominal pain. Awaiting GI consultation. Old myocardial infarction. Allergy to antibiotic agent. Personal history of nicotine dependence or personal history of tobacco use.

*FIG. 13.*

MACHINE LEARNING ENGINE AND RULE ENGINE FOR DOCUMENT AUTO-POPULATION USING HISTORICAL AND CONTEXTUAL DATA

BACKGROUND

Technologies that assist with electronic documentation generally leverage copy-and-paste functionalities, pre-written templates, or hard-coded auto-texts.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

In brief and at a high level, this disclosure describes, among other things, methods, systems, and computer-readable media for automatically identifying, selecting, and auto-populating suggested documentation into a graphical user interface (GUI) for selection, based on determines of a machine learning engine and a rule engine.

In one aspect, a system is provided. The system comprises a machine learning engine that receives a first set of historical data, wherein the first set of historical data is physician-specific patient-encounter data that includes text blocks for a plurality of patient encounters. The machine learning engine generates a first vector from the first set of historical data, wherein the first vector is a physician-specific vector. The machine learning engine also receives a second set of historical data, wherein the second set of historical data is patient-specific context data. Then, the machine learning engine generates a second vector from the second set of historical data, wherein the second vector is a patient-specific vector. The machine learning engine generates a combined vector from the first vector and the second vector, and reduces data sparsity of the combined vector. The machine learning engine continues by generating a plurality of clusters as output from a clustering model, by using the combined vector as input after reducing data sparsity. The plurality of clusters include one or more portions of the physician-specific patient-encounter data or the patient-specific context data. The system also includes a rule engine that identifies a primary cluster in the plurality of clusters that is a best match to the combined vector after reducing data sparsity. In some aspects, the combined vector is supplemented with information about a current encounter, wherein the primary cluster is identified using the supplemented combined vector. The rule engine performs natural language processing of a plurality of text blocks corresponding to the primary cluster. The rule engine also assigns a relevance score for each of the plurality of text blocks in the primary cluster. Then, the rule engine identifies a primary text block in the plurality of text blocks of the primary cluster having a highest relevance score and communicates the primary text block for display as a recommended selection for automatic population of an electronic document.

Another aspect provides one or more non-transitory computer-readable media having computer-executable instructions embodied thereon that, when executed, perform a method. In accordance with the media, a first set of historical data is received and a first vector is generated from the first set of historical data. Further, a second set of historical data is received and a second vector is generated from the second set of historical data. Then, a combined vector is generated from the first vector and the second vector. Data sparsity of the combined vector is reduced and a plurality of clusters are generated. The plurality of clusters are generated as output from a clustering model using the combined vector as input subsequent to reducing data sparsity. The plurality of clusters include the first and second sets of historical data. Continuing, a primary cluster in the plurality of clusters is identified that is a best match to the combined vector, subsequent to reducing data sparsity. In some aspects, the combined vector is supplemented with information about a current encounter and the primary cluster is identified from the supplemented combined vector. Then, natural language processing is performed on the primary cluster and a relevance score is assigned to each of a plurality of text blocks in the primary cluster. A primary text block in the plurality of text blocks of the primary cluster is identified as having a highest relevance score. The primary text block is communicated for display as a recommended selection for automatic population of an electronic document.

Yet another aspect provides one more non-transitory computer-readable media having computer-executable instructions embodied thereon that when executed, via one or more processors, perform a method. In accordance with the media, a first set of historical data is received and a first vector is generated from the first set of historical data. Additionally, a second set of historical data is received and a second vector is generated from the second set of historical data. Then, a combined vector is generated from the first vector and the second vector, and data sparsity of the combined vector is reduced. A plurality of clusters is generated, wherein the plurality of clusters are generated as output from a clustering model using the combined vector as input subsequent to reducing data sparsity, and wherein the plurality of clusters include the first and second sets of historical data. A primary cluster in the plurality of clusters that is a best match to the combined vector is identified subsequent to reducing data sparsity. In some aspects, the combined vector is supplemented with information about a current encounter and the primary cluster is identified for the supplemented combined vector. Then, natural language processing of the primary cluster is performed and a relevance score is assigned to each of a plurality of text blocks in the primary cluster. A primary text block in the plurality of text blocks of the primary cluster is identified as having a highest relevance score. The primary text block is communicated for display as a recommended selection for automatic population of an electronic document.

BRIEF DESCRIPTION OF THE DRAWINGS

Aspects are described in detail below with reference to the attached drawings figures, wherein:

FIGS. 2A-B depict a method in accordance with aspects discussed herein;

FIG. 3 depicts an example of historical patient-specific context data stored in a patient contextual information database, in accordance with aspects discussed herein;

FIG. 4 depicts an example of a combined feature vector generated from historical patient-specific context data of FIG. 3 and historical physician-specific patient-encounter data, in accordance with aspects discussed herein;

FIG. 5 depicts an example of a k-dimensional combined vector with cluster tags generated from the combined feature vector of FIG. 4, in accordance with aspects discussed herein;

FIG. 7 depicts an example graphical user interface in accordance with aspects discussed herein;

FIG. 8 depicts an example feature vector, in accordance with aspects discussed herein;

FIG. 9 depicts examples of text blocks of a primary cluster, in accordance with aspects discussed herein;

FIG. 10 depicts an example of array T and an example of array D generated from the text blocks of FIG. 9, in accordance with aspects discussed herein;

FIG. 11 depicts an example a calculated relevance score based on array T and array D of FIG. 10 for the feature vector of FIG. 8, in accordance with aspects discussed herein;

FIGS. 12 and 13 depict example graphical user interfaces populated with text block suggestions based on relevance scores, in accordance with aspects discussed herein.

DETAILED DESCRIPTION

Figure 1:
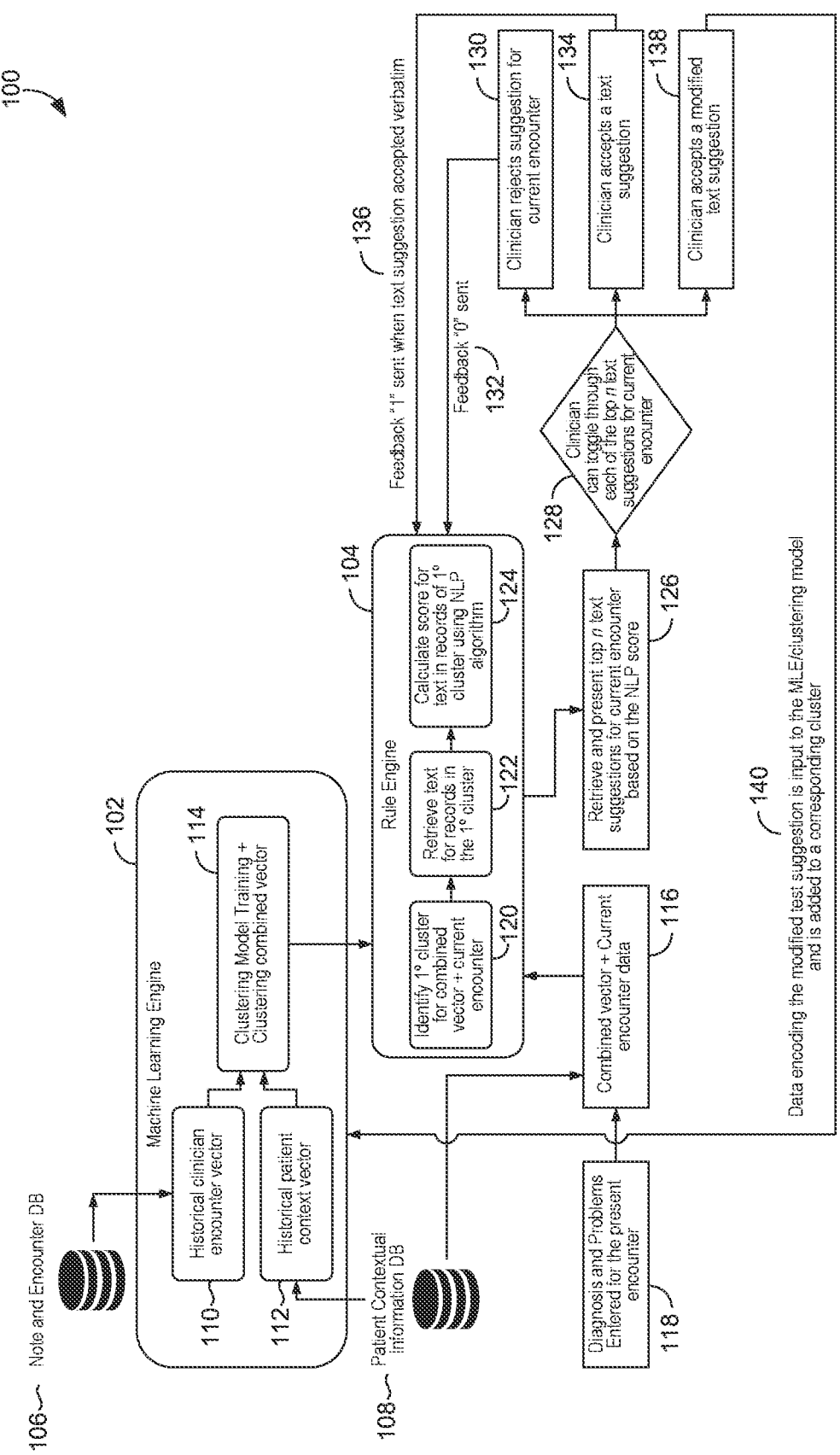
FIG. 1 is a block diagram of an example system, in accordance with aspects discussed herein.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Herein a system, method, and media are provided automatically identify, select, and auto-populate suggested documentation into a graphical user interface (GUI) for selection based on historical data, to facilitate the electronic documentation and entry of factually accurate and contextually relevant text blocks. As used herein, the term "text block" and "document" can be used interchangeably. In order to facilitate the suggestion of factually accurate and contextually relevant text blocks, a machine learning engine builds multiple vectors from historical text data and historical contextual data which are aggregated together into a "combination" vector, that is further processed by the machine learning engine to reduce data sparsity. Then, the machine learning engine inputs the combination vector in order to train a clustering model and to generate clusters representing historical text data and historical contextual data.

Subsequently, using a vector of current and historical contextual data, each cluster is evaluated by a rule engine to evaluated and score the clusters' factual accuracy and contextual relevancy to the vector of current and historical contextual data. The vector of current and historical contextual data corresponds to clinical encounter, in some aspects, for which a text block is to be selected and recommended for entry as electronic documentation. The rule engine identifies one of the clusters as being the most factually relevant and contextually accurate to the vector of current and historical contextual data (e.g., representing a current or past clinical encounter of a particular patient for a specific clinician). From the one "primary" cluster identified by the rule engine, the rule engine further evaluates and scores text data (e.g., blocks of text previously entered by a clinician) using a customized natural language processing algorithm as further described hereinafter. One or more of the text blocks in the primary cluster are chosen by the rule engine as having the highest score(s) relative to the other text blocks within the primary cluster. The selected text block may have a score the meets a minimum threshold, or have the highest n quantity of scores (e.g., the five text blocks having the five highest scores) relative to the other text blocks in the primary cluster, for example. The selected text block(s) are then auto-populated into a graphical user interface for "one-click" entry of the entire text block to facilitate electronic documentation of the current or past clinical encounter of the particular patient for the specific clinician. Once populated, the selected text block can be accepted, rejected, or accepted and edited by a user, through the graphical user interface.

When the particular text block is accepted, rejected, or accepted as edited by a user, this user input or decision is interpreted by the system, method, and media as feedback. This feedback is input to the machine learning engine and/or the rule engine to update (i.e., improve) the clustering and text block scoring for subsequent instances. As such, the machine intelligence improves over time by automatically re-training the clustering model of the machine learning engine and dynamically re-clustering data as new data (e.g., clinician notes, patient contextual data, text block editing) is ingested. Further, the machine intelligence improves over time by updating the natural language processing evaluation performed by the rule engine, to modify scoring to reflect whether, based on the feedback, one or more of the suggested text blocks were selected (i.e., indicating accuracy) or were not selected (i.e., indicating lesser accuracy). This reduces misclassifications of vectors/clusters and/or inaccuracy of suggested text blocks as discussed hereinafter. Because the machine learning engine and the rule engine continue to automatically update and "learn" by ingesting and interpreting user interactions/input as feedback, the factual relevancy and contextual accuracy of suggested text blocks continues to improve with every instance.

The system, method, and media described hereinafter overcome technological limitations of other systems, for example, which are limited to copy-and-paste functionalities pre-written templates, and hard-coded auto-texts. Notably, other systems do not utilize patient contextual data and/or historical data which detrimentally limits their application and lowers accuracy. Also, other systems do not automatically retrain a clustering model/updates cluster and do not automatically update a natural language processing algorithm, for example, based on feedback as interpreted from each instance of user interaction/input. Also, other systems do not improve in factual relevancy and contextual accuracy over time, for example, by ingesting new text data and contextual data into a machine learning engine and/or a rule engine. The aspects of the system, method, and media described hereinafter, in contrast, include these technological improvements that overcome the limitations of copy-and-paste functionalities pre-written templates, and hard-coded auto-texts found in other systems.

Beginning with FIG. 1, a block diagram of a system 100 is provided. A system 100 includes a machine learning engine 102 and a rule engine 104 that are communicatively coupled to each other (e.g., requests, inputs, feedback). In aspects, the system 100 may also include a note and encounter database 106 and a patient contextual information database 108. The note and encounter database 106 and the patient contextual information database 108 may provide data, periodically, intermittently, continuously, at request, or any combination thereof, to the machine learning engine 102 and/or rule engine 104. Although the system 100 is discussed in a clinical application, it should be understood that the system 100 is not limited to such an environment and other applications/environments are contemplated to be within the scope of the invention. As such, the system 100 (and later discussed methods and media) can be implemented in a variety of applications/environments that could benefit from machine learning-based text block suggestions using contextual data and text data.

In various aspects, the machine learning engine 102 receives a first set of historical data. The first set of historical data may be received, retrieved, or obtained from the note and encounter database 106. The first set of historical data is physician-specific patient-encounter data that includes text blocks for a plurality of patient encounters, in some aspects. For example, each text block may include text of any lettering or language input by a clinician to describe a patient encounter, such as, problems, chief complaint(s), diagnoses, classification codes (e.g., ICD-10, SNOMED, LOINC), descriptions of symptoms, medications, primary reason for the clinical encounter, patient history, or any combination thereof. Each text block may include statements that a clinician electronically documents using words, phrases, sentences, paragraphs, numbers, and the like, to form a narrative in the clinical note. In one example, a text block reads: "47-year-old male with mid-abdominal epigastric pain, associated with severe nausea & vomiting; unable to keep down any food or liquid. Pain has become 'severe' and constant. Has had an estimated 13-pound weight loss over the past month. Patient reports eating 12 sausages at the Sunday church breakfast five days ago which he believes initiated his symptoms. Patient admits to a history of alcohol dependence. Consuming 5-6 beers per day now, down from 10-12 per day 6 months ago. States that he has nausea and sweating with 'the shakes' when he does not drink. Allergy to penicillin."

Accordingly, each text block is a narrative input by a clinician to document the reasons and details regarding a clinical encounter with a particular patient, including a patient's medical history and chief complaint, for example. The first set of historical data may include a plurality of text blocks for any number of clinical encounters for any number of patients; however the first set of historical data generally corresponds to one clinician. As such, the first set of historical data is being received, retrieved, or obtained for a particular clinician using a clinical identifier, for example. However, it is contemplated that the first set of historical data may be retrieved for a plurality of clinicians, for example, that all share a related specialty, clinic, location, or other characteristic such that the first set of historical data need not be limited to just one clinician in every instance.

In various aspects, a patient identifier is also associated with each text block for various clinical encounters is retrieved in the first set of historical data. As such, the patient identifier(s) can be mapped to a second set of historical data, as further discussed below with regard to patient-specific context data.

The machine learning engine 102 generates a first vector from the first set of historical data, shown at 110, and as such, the first vector is a physician-specific vector, in various aspects. However, in aspects where the first set of historical data may be retrieved for a plurality of clinicians, for example, the first vector may represent the group and be a group-specific vector that represents clinical encounters for the group (e.g., orthopedic specific, obstetrics specific, neuro-oncology specific, acute care specific, ambulatory care specific, rehabilitation specific).

The machine learning engine 102 receives a second set of historical data, wherein the second set of historical data is patient-specific context data. The second set of historical data may be received, retrieved, or obtained from the patient contextual information database 108. An example of patient-specific context data is shown in FIG. 3, which illustrates data stored the patient contextual information database 108. The patient-specific context data may include, for example, data encoding demographic and/or historical clinical characteristics for a plurality of a patients. In some instances, the patient-specific context data is retrieved as encoding demographic and/or historical clinical characteristics for one particular patient. As such, the second set of historical data is being received, retrieved, or obtained for a particular patient using a patient identifier, for example. However, it is contemplated that the second set of historical data may be retrieved for a plurality of patients, for example, that all share a related specialty, clinic, location, or other characteristic such that the second set of historical data need not be limited to just one patient in every instance.

In various aspects, the patient-specific context data may include, for example, age, gender, ethnicity, weight, height, location (e.g., geographical tag), allergies, problems, diagnosis, chief problem, patient history, or any combination thereof. The machine learning engine 102 generates a second vector from the second set of historical data, shown at 112. The second vector may be a one-hot-encoded array, in some instances. In some aspects, the second vector is a patient-specific vector, in some aspects. In other aspects, the machine learning engine 102 generates a second vector from the second set of historical data, but the second vector is specific to a group of patients having one or more shared characteristics in the patient-specific context data. In some aspects, the second vector may be generated using the patient-specific context data that also includes one or more classification codes (e.g., ICD-10, SNOMED, LOINC). Classification codes can be obtained by mapping a unique patient identifier in the patient-specific context data to a patient identifier also stored in association with the physician-specific patient-encounter data, and thus locating narratives for one or more encounters that correspond to the unique patient identifier.

Continuing, the machine learning engine 102 generates a combined feature vector (interchangeably referred to a "combined vector") using the first vector and the second vector. As such, the combined feature vector includes data and/or represents data obtained from both the first and second historical data sets, in aspects. When generating the combined feature vector, quantitative values (i.e., "continuous" values) generally captured from the first and second vectors as-is, and are retained. However, the machine learning engine 102 identifies, in some aspects, that the first and/or second vector may include discrete categorical data from one or more of the first set of historical data or the second set of historical data. In such aspect, the machine learning engine specifically identifies the categorical data because the categorical data is incompatible to be input to a clustering model. The machine learning engine 102 transforms identified categorical data into dummy variables, wherein the dummy variables are used in the combined feature vector because the dummy variables are compatible as input to a clustering model. Generally, a "dummy variable" takes only a value of "0" or "1" to indicate the absence or presence of a categorical effect (e.g., "1" to indicate a smoker and "0" to indicated a non-smoker in a category "tobacco use"). In this manner, a dummy variable can act as a substitute for the categorical data, for example, within a model that sorts data. FIG. 4 depicts an example of a combined feature vector that has been generated from a second vector (e.g., created from patient contextual information database information shown in the example of FIG. 3) in combination with a first vector (e.g., created from physician-specific patient-encounter data extracted from the note and encounter database 106). Generally, a vector can be represented using an array of numerical values.

In general, a combined feature vector grows in dimensionality, as a column is added for each feature or field and a row is added to contain values (e.g., "0" absent; "1" present) for each record. As used herein, "feature" and "field" can be used interchangeably. For example, each feature (e.g., gender, ethnicity, problem, ICD-10 code, weight) obtained from the first and second historical data sets (e.g., patient-specific context data and the physician-specific patient-encounter data) corresponds to a column in the combined feature vector, and each record obtained from the first and second historical data sets (e.g., patient-specific context data and the physician-specific patient-encounter data) corresponds to a row in the combined feature vector. Under each column for a feature, a value of "1" indicates that the record for that row has data that is related to the feature, whereas a value of "0" indicates that the record does not have data that is related to the feature (i.e., data for that feature is absent, lacks data for that features). Accordingly, the combined feature vector has n dimensions (e.g., "n" refers to the total quantity), one dimension for each of a plurality of features.

As the combined vector increases in dimensionality, computational time increases. As such, the machine learning engine 102 reduces data sparsity of the combined vector in order to decrease the dimensionality of the combined vector and decrease computational times associated with the vector, in aspects. To reduce the data sparsity of the combined vector, the machine learning engine 102 removes columns that only include values of "0" in the rows for that columns, and further removes rows that only include values of "0," in some aspects. This decreases the total quantity of columns and/or rows, thus reducing the total dimensionality of the combined vector. In aspects, the machine learning engine 102 applies a Principle Component Analysis (PCA) to the combined vector to identify sparse columns of the combined vector. In one such aspect, the combined vector can having n dimensions is projected to a k dimensional vector space to reduce a total quantity of the sparse columns/rows, wherein k is less than n (i.e., k<<n) in quantity. After data sparsity reduction, the k-dimensional combined vector is passed to a clustering module of the machine learning engine 102.

The clustering module of the machine learning engine 102 generates a plurality of clusters by training the clustering model, using the k-dimensional combined vector as input, shown at 114. In such aspects, the plurality of clusters are generated as output from the clustering model, using the k-dimensional combined vector as input. The plurality of clusters correspond to or include one or more portions of physician-specific patient-encounter data or patient-specific context data of the k-dimensional combined vector. In some aspects, when generating the plurality of clusters, a total quantity of the plurality of clusters is determined by one or more characteristics of the first and second sets of historical data in the k-dimensional combined vector, as generated from the first and second vectors. A plurality of cluster tags are attached to the k-dimensional combined vector, in some aspects, wherein each cluster tag maps a feature or record from one or more of the first and second sets of historical data to one or more of the plurality of clusters. FIG. 5 depicts an example of a k-dimensional combined vector with cluster tags that have been assigned to each record under a new column (e.g., cluster identifier "CI").

In one aspect, the clustering model is a Density-Based Spatial Clustering of Applications with Noise (DBSCAN) model. When generating the clusters, the clustering model may be tuned to produce clusters defined with particular parameters. In various aspects, the clustering model may define a maximum allowed distance between two samples for the two samples to be considered to be in the same cluster or "neighborhood." Additionally or alternatively, the clustering model may be tuned, in some aspects, to require a minimum quantity of samples (or total weight) to be used to form a cluster for any point to considered a "core" point, inclusive of the point itself. Using such examples, the k-dimensional combined vector is input to a DBSCAN model as training the model and clustering the data into a defined total quantity of clusters. The total quantity of clusters produced can be determined, in some aspects, based on the features (e.g., columns) of the k-dimensional combined vector. Based on the clusters generated, a cluster tag can be attached to each record (e.g., rows) of the k-dimensional combined vector to represent which cluster(s) that record corresponds to according to the model. Having generated a plurality of clusters, the k-dimensional combined vector or the non-reduced combined vector, as well as the trained clustering model, can be accessed by and/or communicated to the rule engine 104.

The rule engine 104 can access the trained clustering model. Further, the rule engine 104 receives the k-dimensional combined vector or the non-reduced combined vector, in various aspects. In some aspects, the k-dimensional combined vector or the non-reduced combined vector received by the rule engine 104 is as previously described, but includes additional data representing one or more diagnoses and/or one or more problems defined for or associate with a current clinical encounter, shown at 116 and 118. As such, the k-dimensional combined vector or the non-reduced combined vector that is input to the rule engine 104 can include contextual information from prior encounters (i.e., as explained above regarding the first and second sets of historical data) and contextual information for a present or current encounter, in some aspects. When a non-reduced combined vector is received by the rule engine 104, the rule engine 104 transforms the non-reduced combined vector into a k-dimensional combined vector, as previously described.

The rule engine 104 inputs the k-dimensional combined vector, as supplemented with contextual information for a present or current encounter, into the trained clustering model in order to identify a primary cluster in the plurality of clusters that is a best match to the k-dimensional combined vector, shown at 120. As such, in various aspects, the rule engine 104 identifies the primary cluster in the plurality of clusters that is a "best" match to the combined vector (supplemented) 116 by identifying one cluster in the plurality of clusters that corresponds to a set of text blocks in one or more of the physician-specific patient-encounter data or patient-specific context data, wherein that set of text blocks in the one cluster exhibits the greatest similarity to the k-dimensional combined vector, as supplemented, relative to other clusters in the plurality of clusters. As such, the k-dimensional combined vector, as supplemented, is input to the clustering model to determine what cluster the k-dimensional combined vector, as supplemented, should be sorted into, or "belongs" to according to the trained clustering model. Then, in such an aspect, the rule engine 104 designates the one cluster as the primary cluster based on the one cluster have the greatest similarity to the k-dimensional combined vector, as supplemented to represent the present or current encounter. As further discussed below, text blocks are to be suggested by the rule engine 104 specifically for the present or current encounter.

After identifying the primary cluster, the rule engine 104 performs natural language processing on a plurality of text blocks that correspond to the records that belong to or are "in" the primary cluster. For example, the rule engine 104 retrieves the actual text block data for each of the records sorted into the primary cluster, shown at 122. In some aspects, the cluster tags that were added into the k-dimensional combined vector by the machine learning engine 103 are used by the rule engine 104 to locate the corresponding records belonging to the primary cluster. The entirety of the text data for these records can be retrieved from the note and encounter database 106, as text blocks or blocks of texts (i.e., a clinical narrative or note), in various aspects. The rule engine 104 calculates and assigns a relevance score to each of the plurality of text blocks retrieved that correspond to the records in the primary cluster, shown at 124, in an aspect. For example, the rule engine 104 uses natural language processing to score the plurality of text blocks that were retrieved for the records sorted into the primary cluster for their factual accuracy and/or contextual relevance to the present or current encounter represented in the k-dimensional combined vector, as supplemented. For each text block, the rule engine 104 calculates Term Frequency ("TF") of each term "t" in that text block, shown below. For each text block "d," the rule engine 104 further calculates Inverse Document Frequency ("IDF"), shown below.

$$\text{Term Frequency } (t, d) = \frac{\text{freq of the term } t \text{ in document } d}{\text{total number of terms in document } d}$$

$$\text{Inverse Document Frequency } (t) =$$
$$\log \frac{\text{total number of documents in the identified cluster}}{\text{total number of documents that have the term } t \text{ in them}}$$

In aspects, one or more classification codes for one or more diagnoses or problems are identified by the rule engine as terms, and these classification codes are stored in array "T." "Classification code" and "term" are referred to interchangeably regarding the actions of the rule engine 104. For example, the rule engine 104 creates array T=[234789008, 67899009, A34.988E] to store a plurality, or all, of the classification codes identified in that text block. In various aspects, one or more of, or all of, the plurality of text blocks that were retrieved for the records sorted into the primary cluster are stored by the rule engine 104 in array "D" (i.e., the text data of the text block is itself is stored in array D). The rule engine 104 calculates the Term Frequency and the Inverse Document Frequency of each classification code that is present or stored in array T. Based on those determination, the rule engine 104 calculates "TF-IDF" for each classification code present in array T, shown below. For each classification code in array T, the calculated TF-IDF is determined to be the "score" that associated with and/or that is assigned by the rule engine 104 to the corresponding text block present in or stored in array D.

$$\text{TF-IDF} = \text{Term Frequency}(t,d) * \text{Inverse Document Frequency}(t)$$

In aspects, for each text block in array D, the rule engine 104 calculates a Relative Term Relevance (RTR) for each classification code in array T, where RTR is calculated for that code relative to the other classification codes in array T, as shown below.

$$\text{Relative Term Relevance } (t, d) = \frac{\text{number of times the term } t \text{ is present in document } d}{\sum_{i=1}^{length(T)} \text{number of times term } t(i) \text{ is present in document } d}$$

An array D-tagged is generated by the rule engine 104 that stores the text blocks with each text block's corresponding relevance score attached to said text block.

In some aspects, array T, array D, and array D-tagged are generated and calculated as discussed above, and are utilized as input for the following algorithm to determine and calculate the relevance score, using both TF-IDF and RTR, shown below.

num_d=number of documents in D
    initialize D_tagged=empty array for num_d number of items
    num_t=number of terms in T
    for d∈ 1 . . . num_d do
        initialize document_relevance_score=0
        for t∈ 1 . . . num_t do
            term_relevance_score=TF(t, d)*IDF(t)*RTR(t, d)
            document_relevance_score=document_relevance_score+term_relevance_score
        D_tagged[d]=(D[d], document_relevance_score)

Accordingly, the rule engine 104 then identifies a primary text block in the plurality of text blocks of the primary cluster, wherein the primary text block is determined by the rule engine 104 to have the highest relevance score relative to each of the other text blocks in the primary cluster. The primary text block is selected based on at least one of the TF-IDF and/or RTR of that text block, as shown above. In aspects, the rule engine 104 may further identify and select a "top" n quantity of text blocks (e.g., top 3, top 5, top 10) that have the highest scores when ranked relative to the other text blocks corresponding to the primary cluster. The primary text block and one or more of the next highest scoring text blocks, in such instances, may be stored in an new array by the rule engine 104 for further accessibility.

The rule engine 104 retrieves the primary text block and communicates the primary text block for display as a suggestion or recommendation, so that the primary text block can optionally be selected. If selected, the primary text block is automatically populated into a GUI, input box, and/or other type of electronic documentation, shown at 126. Further, as shown at 126, the rule engine 104 can also retrieve one or more of the next highest scoring text blocks (e.g., second highest score, third highest score, fourth highest score, and nth highest score) and communicates the primary text block and the next highest scoring text blocks for display as suggestions or recommendations. A user (e.g., a clinician) can browse through a sequence of the primary text block and the secondary text blocks (e.g., top n quantity of the highest scored text blocks) being suggested for selection, shown at 128, in the example of FIG. 1.

In some aspects, user input is received that does not select the primary text block, shown at 130. In such an aspect, when the user input does not select the primary text block for automatic population of the electronic document, a value of zero (e.g., numerical/binary value of "0") is communicated to a rule engine 104 as feedback for subsequent cluster identifications of primary and/or secondary text blocks in other encounters, shown at 132. With each interaction (i.e., non-selection), the scoring accuracy of the rule engine 104 increases, thus the rule engine 104 provides increasingly accurate text block suggestions for subsequent encounters.

In some aspects, user input is received that selects the primary text block, shown at 134. In such an aspect, when the user input is a selection of the primary text block for automatic population of the electronic document, a value of one (i.e., numerical/binary value of "1") is communicated to a rule engine 104 as feedback for subsequent cluster identifications, shown at 136. As such, the feedback increases the scoring accuracy of the rule engine 104 for subsequent instances. With each interaction (i.e., selection), the scoring accuracy of the rule engine 104 increases thus the rule engine 104 provide increasingly accurate text block suggestions.

In some aspects, shown at 138, user input is received that includes an edited version of the primary text block. In such an aspect when the user input is a selection of an edited version of the primary text block for automatic population of the electronic document, the edited version of the primary text block is communicated to a machine learning engine, wherein the edited version is stored as new historical data, shown at 140. Further, the edited version of the primary text block is attached to the combined vector, and this combined vector with the attachment (i.e. the modified text data itself) is input to the machine learning engine 102. In this manner, the clustering accuracy of the machine learning engine 102 is increased for subsequent determinations due to the ingestion of the new contextual data (e.g., the modified text data) and affirmation (selection) via the combined vector with the attachment, for each new instance received.

It should be understood from this description that the system 100 can operate to concurrently provide text block recommendations to any quantity of clinicians, for any quantity of encounters, in near real-time, in a distributed healthcare environment, such that the system 100 serves up suggestions customized for each encounter, based on the particular clinician and patient involved in that encounter, at a vast scale. The clustering model may be updated periodically, in some instances, while the rule engine 104 can make determinations for each next clinical encounter that is scheduled, for example.

Having described the system 100 and components thereof, it will be understood by those of ordinary skill in the art that system 100 is but one example of a suitable system and is not intended to limit the scope of use or functionality of the present invention. Similarly, system 100 should not be interpreted as imputing any dependency and/or any requirements with regard to each component and combination(s) of components illustrated in FIG. 1. It will be appreciated by those of ordinary skill in the art that the location of components illustrated in FIG. 1 is an example, as other methods, hardware, software, components, and devices for establishing a communication links between the components shown in FIG. 1, may be utilized in implementations of the present invention. It will be understood to those of ordinary skill in the art that the components may be connected in various manners, hardwired or wireless, and may use intermediary components that have been omitted or not included in FIG. 1 for simplicity's sake. As such, the absence of components from FIG. 1 should be not be interpreted as limiting the present invention to exclude additional components and combination(s) of components. Moreover, though components are represented in FIG. 1 as singular components, it will be appreciated that some aspects may include a plurality of devices and/or components such that FIG. 1 should not be considered as limiting the number of a device or component.

Figure 2A:
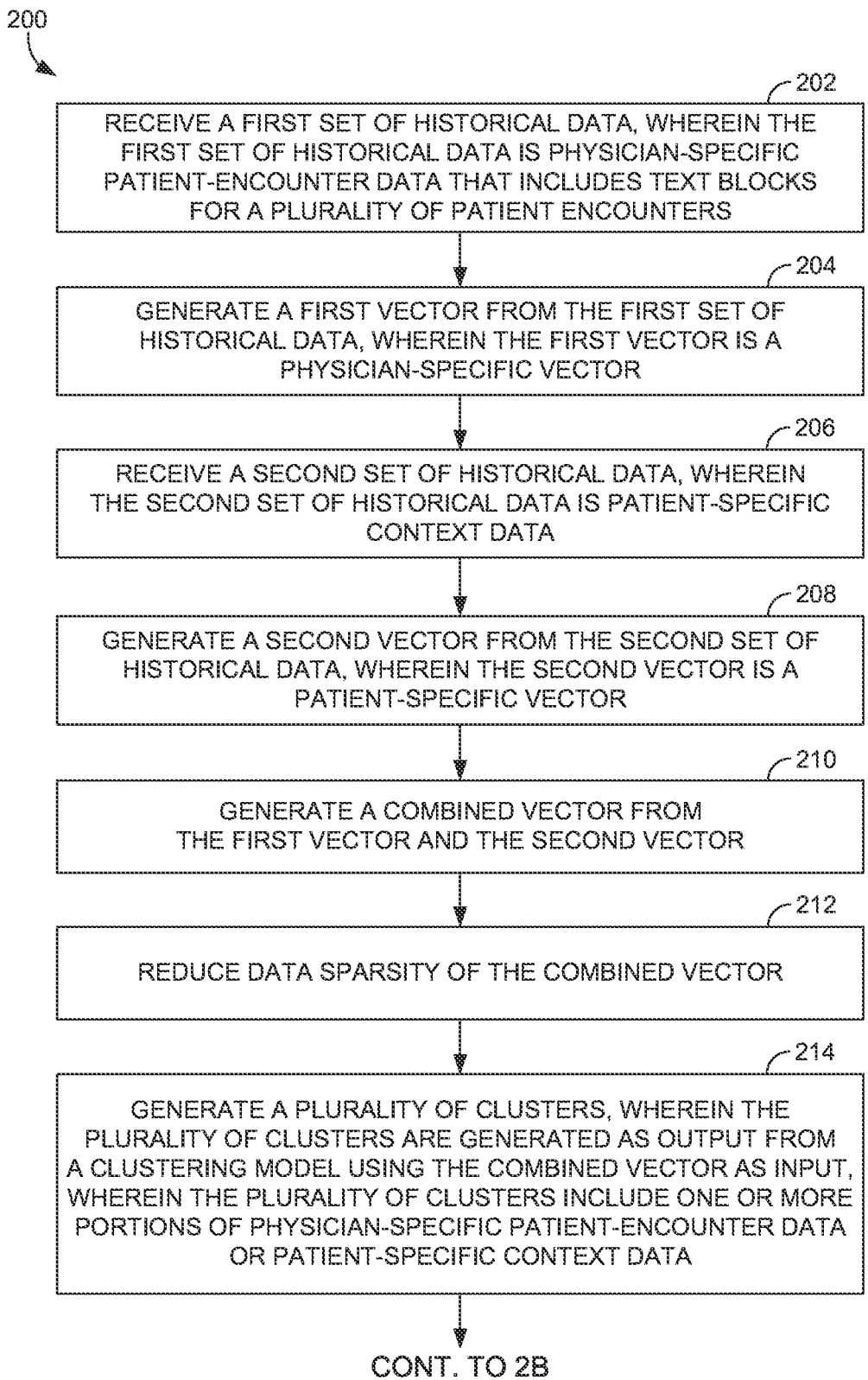

Continuing to FIG. 2A-B, a method 200 is provided. In some aspects, the method 200 can be a computer-implemented method. In aspects, one or more non-transitory computer-readable storage media having computer-readable instructions or computer-readable program code portions embodied thereon, for execution via one or more processors, can be used to implement and/or perform the method 200. For example, computer-readable instructions or computer-readable program code portions can specify the performance of the method 200, can specify a sequence of steps of the method 200, and/or can identify particular component(s) of a software and/or hardware for performing one or more of the steps of the method 200, in aspects. The computer-readable instructions or computer-readable program code portions can correspond to a machine learning engine and a rule engine, as previously discussed. In one aspect, an application programming interface (API) can implement and/or perform the method 200, using the machine learning engine and a rule engine discussed. As discussed below, the method 200 can be performed using software, hardware, component(s), and/or device(s) depicted in the example of FIG. 1. For example, one or more steps of the method 200 can be performed at a user device, using one or more processors of the user device, to support an application. Further, as aspects of the method 200 have been previously described above with regard to the component(s) of the system 100 of FIG. 1, the steps are discussed with brevity.

At block 202, a first set of historical data is received. Then, at block 204, a first vector is generated from the first set of historical data. In some aspects, the first set of historical data is physician-specific patient-encounter data and the first vector that is generated is a physician-specific vector. At block 206, a second set of historical data is received. Then, at block 208, a second vector is generated from the second set of historical data. The second set of historical data is patient-specific context data, wherein the second vector is a patient-specific vector. At block 210, a combined vector is generated from the first vector and the second vector. To generate the combined vector, discrete categorical data is identified in one or more of the first set or the second set of historical data, wherein the categorical data is incompatible for input to the clustering model. The categorical data is transformed into dummy variables, such that the dummy variables are used to generate the combined vector as being compatible for input to the clustering model.

At block 212, data sparsity of the combined vector is reduced. Reducing data sparsity of the combined vector can include, for example, applying Principle Component Analysis (PCA) to the combined vector to identify sparse columns of the combined vector. In various aspects, the combined vector has n dimensions, i.e., one dimension for each of a plurality of features. Then, by projecting the combined vector having n dimensions to a k dimensional vector space, the total quantity of columns is reduced (i.e., the sparse columns are removed), wherein k<n.

Continuing to block 214, a plurality of clusters are generated, wherein the plurality of clusters are generated as output from the clustering model using the k-dimensional combined vector as input. As such, the plurality of clusters include the first and second sets of historical data, integrated by way of the first and second vector being combined. In some aspects, the first set of historical data is physician-specific patient-encounter data such that the first vector is a physician-specific vector, and the second set of historical data is patient-specific context data such that the second vector is a patient-specific vector. In such an aspect, the plurality of clusters includes one or more portions of physician-specific patient-encounter data or patient-specific context data, for example, based on a clustering model being applied to and/or trained using the k-dimensional combined vector. In one or more aspects, the clustering model is a Density-Based Spatial Clustering of Applications with Noise (DBSCAN). When generating the plurality of clusters, a total quantity of the plurality of clusters may be determined by one or more characteristics of the first and second sets of historical data in the k-dimensional combined vector, for example. In an aspect, a plurality of cluster tags can be attached to the k-dimensional combined vector, wherein the plurality of cluster tags map features of the first and second sets of historical data to one or more of the plurality of clusters.

At block 216, a primary cluster is identified that is a best match to the combined vector for a current encounter. For example, one cluster in the plurality of clusters that corresponds to text blocks in one or more of the physician-specific patient-encounter data or patient-specific context data (e.g., first and second sets of historical data) is identified, wherein the text blocks in the one cluster have a greatest similarity to the k-dimensional combined vector relative to other clusters in the plurality of clusters. In such an example, the one cluster is assigned, designated, or selected as the primary cluster based on the one cluster have the greatest similarity to the k-dimensional combined vector. Then, at block 218, natural language processing of the primary cluster is performed. Further, at block 220, a relevance score is assigned for each of a plurality of text blocks in the primary cluster. At block 222, a primary text block having a highest relevance score is identified in the plurality of text blocks of the primary cluster. At block 224, the primary text block is communicated for display as a recommended selection for automatic population of an electronic document.

Figure 6A:
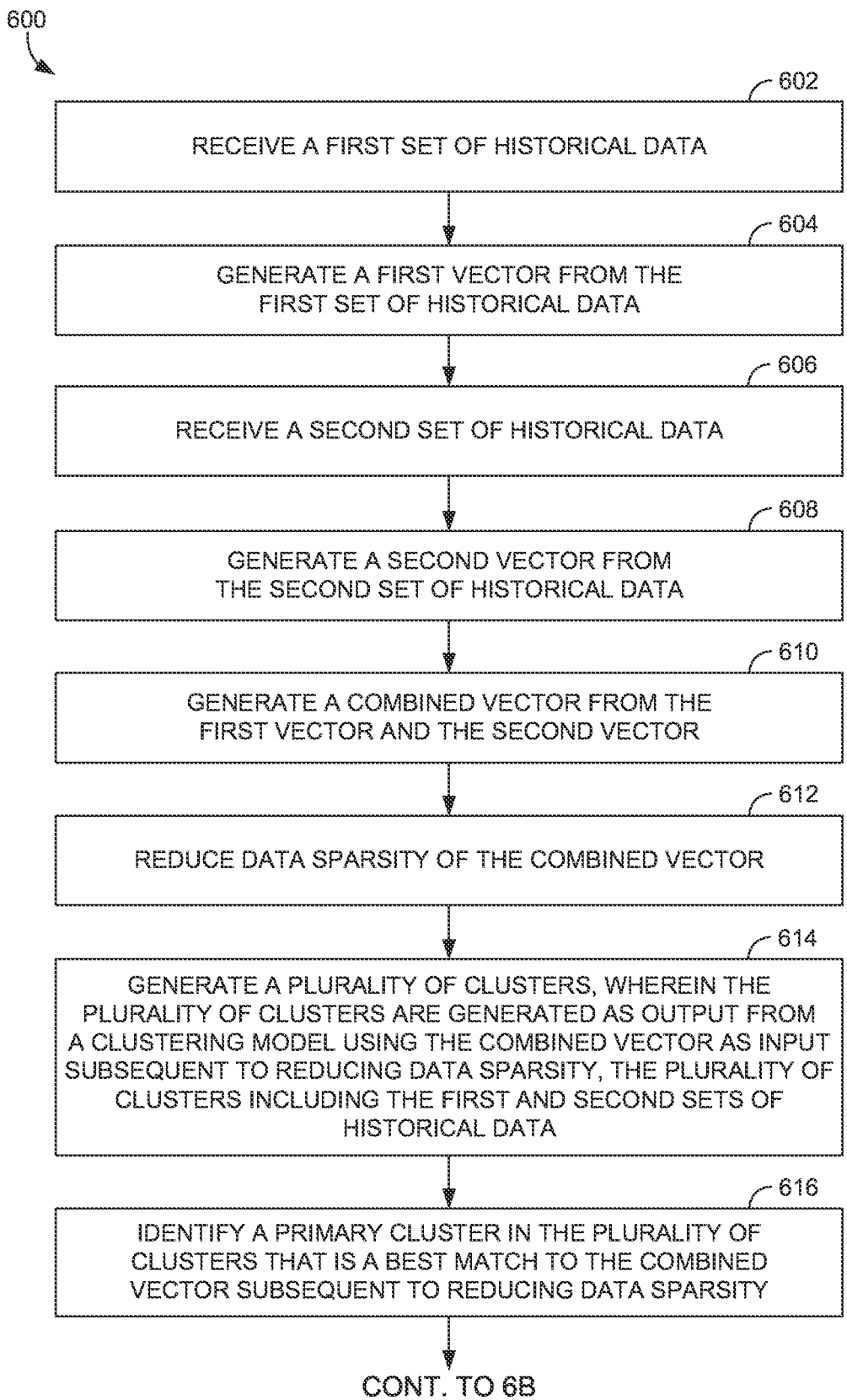
FIGS. 6A-B depict a method in accordance with aspects of the present invention.
Figure 6B:
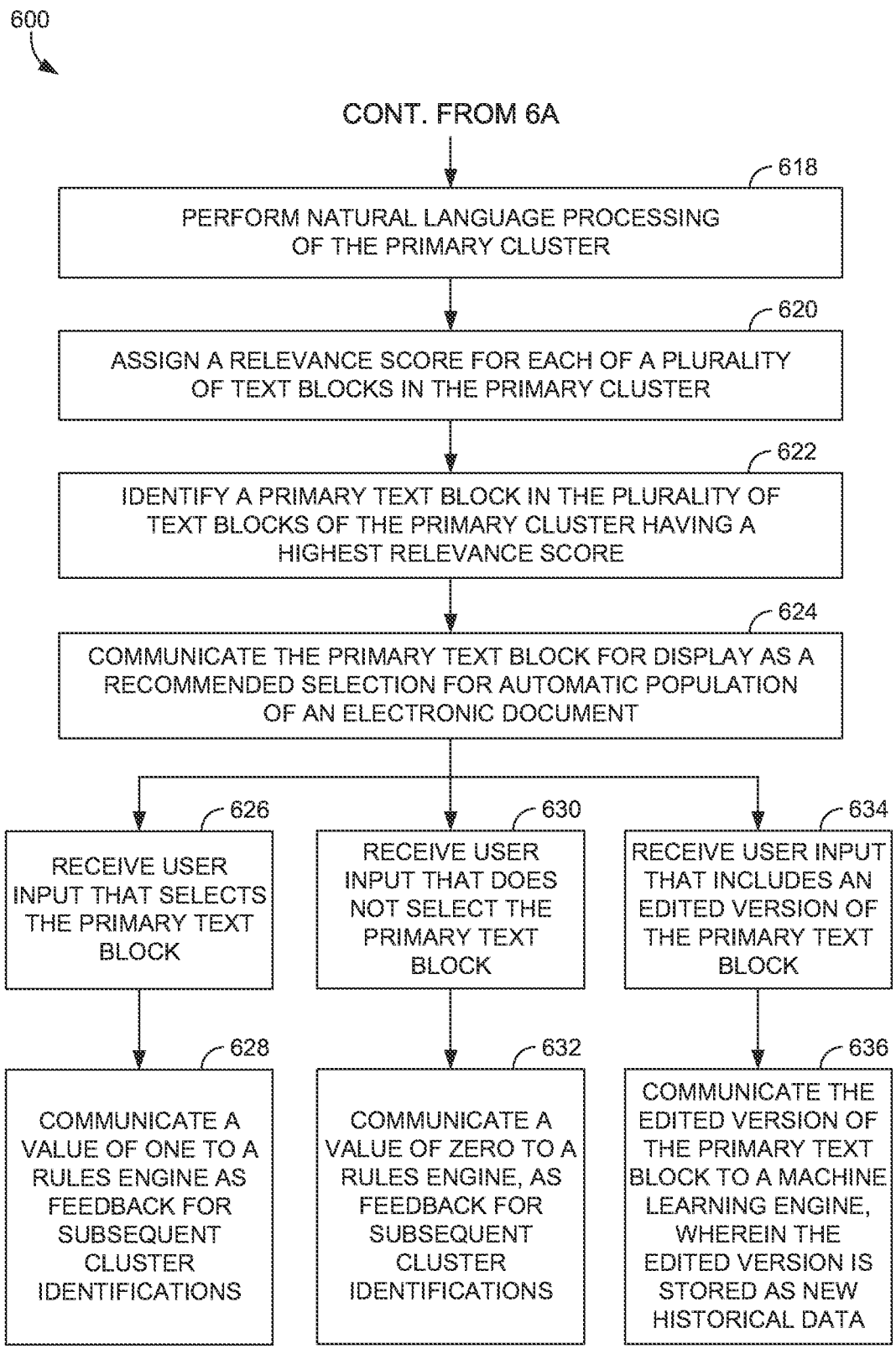

Turning now to FIG. 6A-B, a method 600 is provided. In aspects, the method 600 can be a computer-implemented method. In one aspect, one or more non-transitory computer-readable storage media having computer-readable instructions or computer-readable program code portions embodied thereon, for execution via one or more processors, can be used to implement and/or perform the method 600. For example, computer-readable instructions or computer-readable program code portions can specify the performance of the method 600, can specify a sequence of steps of the method 600, and/or can identify particular component(s) of a software and/or hardware for performing one or more of the steps of the method 600, in aspects. The computer-readable instructions or computer-readable program code portions can correspond to an application and/or an application programming interface (API), in some aspects. In one aspect, the application or API can implement and/or perform the method 600. As discussed below, the method 600 can be performed using software, hardware, component(s), and/or device(s) depicted in the example of FIG. 1. For example, one or more steps of the method 600 can be performed at a user device, using one or more processors of the user device, to support an application. Further, as aspects of the method 600 have been previously described above with regard to the component(s) of the system 100 of FIG. 1, the steps are discussed with brevity.

At block 602, a first set of historical data is received. Then at block 604, a first vector is generated from the first set of historical data. At block 606, a second set of historical data is received. Then, at block 608, a second vector is generated from the second set of historical data. Continuing, shown at block 610, a combined vector is generated from the first vector and the second vector. At block 612, data sparsity of the combined vector is reduced. At block 614, a plurality of clusters is generated, wherein the plurality of clusters are generated as output from a clustering model using the combined vector as input subsequent to reducing data sparsity, the plurality of clusters include the first and second sets of historical data.

For example, FIG. 7 depicts an example GUI 700 that displays a chief complaint of a current patient encounter associated with a particular clinician, as well as a history of the patient's present illness. The GUI 700 includes a input box "Assessment and Plan" into which the rule engine 104 can input a suggested text block for entry, based on k-dimensional combined vector. In FIG. 7, the classification codes of one or more diagnoses and/or problems are identified from the "Chief Complaint": "My stomach hurts and I feel full of gas" corresponds to [Abdominal pain (R10.9), Gastritis (K29.20)]. Further, based on the "History of Present Illness," classification codes of one or more diagnoses and/or problems are identified such as [Nausea with vomiting (R11.2), Alcohol Dependence (F10.29), Penicillin Allergy (Z88.0)]. Further, patient contextual data is obtained, for example: Age 47; Weight 146 lbs; Gender Male. Using this information, a vector is created for the patient for that encounter, as shown in FIG. 8, albeit clinician-specificity has not yet been added. It will be understood that the vector has been greatly simplified for this discussion, as in practice, the vector would include many more columns/features and rows/records. The vector can then be reduced in data sparsity.

Continuing with the method 600 at block 616, subsequent to reducing data sparsity, a primary cluster is identified in the plurality of clusters that is a best match to the combined vector. As shown in FIG. 6B at block 618, natural language processing of the primary cluster is performed. At block 620, a relevance score is assigned for each of a plurality of text blocks in the primary cluster. Then, at block 622, a primary text block in the plurality of text blocks of the primary cluster is identified as having a highest relevance score. At block 624, the primary text block is communicated for display as a recommended selection for automatic population of an electronic document.

To illustrate, and assuming the vector of FIG. 8 is completed with clinician specificity and is k-dimensional, a primary cluster is identified as corresponding that vector. The primary cluster corresponds to records, and those records includes text blocks: Block 1 and Block 2 shown in FIG. 9. In this example, FIG. 10 depicts an example term array T and example document array D generated from Block 1 and Block 2 by a rule engine, from the primary cluster. The records in the primary cluster include clinician-specific note and encounter data, shown as Block 1 and Block 2. In accordance with this example, FIG. 11 depicts a calculation of a relevance score for Block 2 relative to the vector of FIG. 8 for the current encounter. In this example, Block 2 is determined to have a relevance score of 0.0751, and array D-tagged thus stores Block 2 as tagged with this corresponding score. Further in this example, Block 1 is determined to have a relevance score of 0.0602 (not shown), and array D-tagged thus stores Block 1 as tagged with this corresponding score, per the rule engine. In this example, Block 2 has a higher relevance score than Block 1 and thus is selected by the rule engine to be the primary text block that is communicated for display. FIG. 12 depicts an example GUI 1200 that has been automatically populated with text Block 2 as the primary text block suggestion. In various aspects, the top n quantity of highest scoring (i.e., most factually accurate and contextually relevant) text blocks in the primary cluster are stored in an array that is used by the rule engine to populate suggestions into the GUI 1200. In one example, a user can interact with the GUI 1200, for example by clicking a button or typing a shortcut (Ctrl+F2) to cause the automatic display of each of the top n quantity of most relevant text blocks within the input box "Assessment and Plan," in sequence from the highest scoring (i.e., most relevant) text block to the least scoring text block of the top n quantity of most relevant text blocks in the primary cluster as stored in the array. FIG. 13 depicts an example GUI 1300 that has been automatically populated the content of Block 1 within the input box "Assessment and Plan" as a secondary text block suggestion, in response to a user interacting with the GUI to toggle between n suggested text blocks for selection.

Turning back to the method 600, in some aspects, as shown at block 626, user input is received that selects the primary text block. In such an aspect, when the user input is a selection of the primary text block for automatic population of the electronic document, shown at block 628, a value of one (i.e., numerical/binary value of "1") is communicated to a rule engine as feedback for subsequent cluster identifications.

In some aspects, shown at block 630, user input is received that does not select the primary text block. In such an aspect, when the user input does not select the primary text block for automatic population of the electronic document, shown at block 632, a value of zero (e.g., numerical/binary value of "0") is communicated to a rule engine, as feedback for subsequent cluster identifications.

In some aspects, shown at 634, user input is received that includes an edited version of the primary text block. In such an aspect when the user input is a selection of an edited version of the primary text block for automatic population of the electronic document, shown at block 636, the edited version of the primary text block is communicated to a machine learning engine, wherein the edited version is stored as new historical data.

In each instance where user input is received, for example, the selections made by a user as well as what is not selected (e.g., rejected or unselected) via the user inputs is interpreted and used as feedback that improves the factual relevance and contextual accuracy of one or more subsequent and future text blocks that are identified and chosen to be provided as suggestions/recommendations, in accordance with the method 600.

Figure 14:
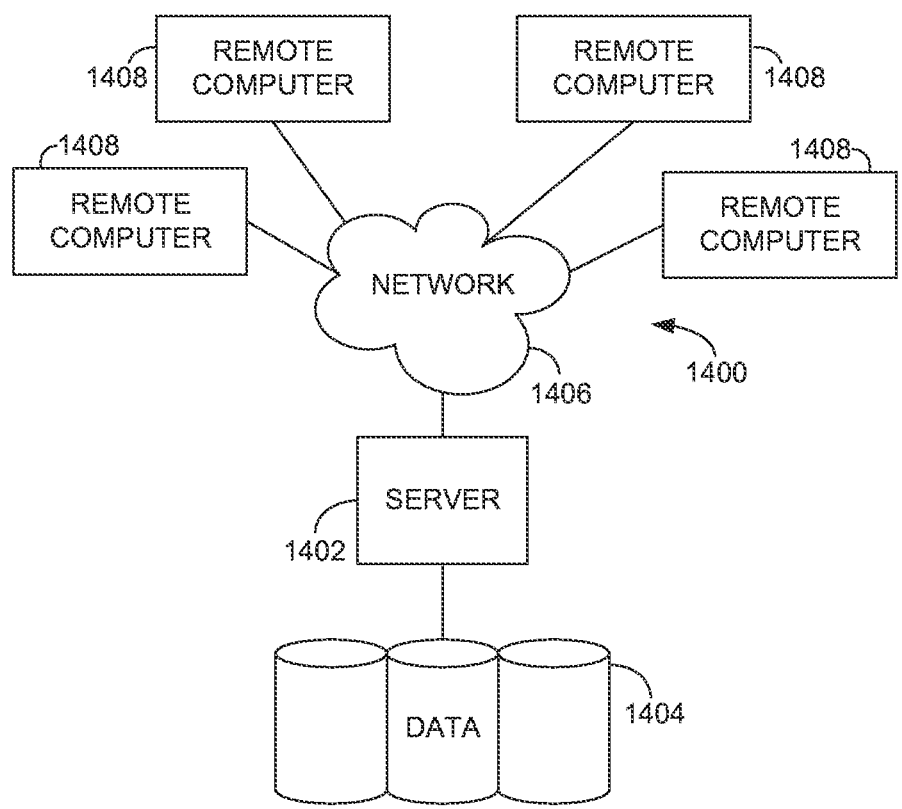
FIG. 14 depicts an example computing environment suitable for implementing aspects discussed herein.

Turning now to with FIG. 14, an example of a computing environment 1400 is depicted, in accordance with an aspect of the present invention. It will be understood by those of ordinary skill in the art that the computing environment 1400 is just one example of a suitable computing environment and is not intended to limit the scope of use or functionality of the present invention. Similarly, the computing environment 1400 should not be interpreted as imputing any dependency and/or any requirements with regard to each component and combination(s) of components illustrated in FIG. 14. It will be appreciated by those having ordinary skill in the art that the connections illustrated in FIG. 14 are also exemplary as other methods, hardware, software, and devices for establishing a communications link between the components, devices, systems, and entities, as shown in FIG. 14, may be utilized in implementation of the present invention. Although the connections are depicted using one or more solid lines, it will be understood by those having ordinary skill in the art that the exemplary connections of FIG. 14 may be hardwired or wireless, and may use intermediary components that have been omitted or not included in FIG. 14 for simplicity's sake. As such, the absence of components from FIG. 14 should be not be interpreted as limiting the present invention to exclude additional components and combination(s) of components. Moreover, though devices and components are represented in FIG. 14 as singular devices and components, it will be appreciated that some aspects may include a plurality of the devices and components such that FIG. 14 should not be considered as limiting the number of a device or component.

Continuing, the computing environment 1400 of FIG. 14 is illustrated as being a distributed environment where components and devices may be remote from one another and may perform separate tasks. The components and devices may communicate with one another and may be linked to each other using a network 1402. The network 1402 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 1402, generally, provides the components and devices access to the Internet and web-based applications.

The computing environment 1400 includes a computing device 1404, which may be in the form of a server. Although illustrated as one component in FIG. 14, the present invention may utilize a plurality of local servers and/or remote servers in the computing environment 1400. The computing device 1404 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The computing device 1404 may include or may have access to computer-readable media. Computer-readable media can be any available media that may be accessed by computing device 1404, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the computing device 1404. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In aspects, the computing device 1404 uses logical connections to communicate with one or more remote computers 1406 within the computing environment 1400. In aspects where the network 1402 includes a wireless network, the computing device 1404 may employ a modem to establish communications with the Internet, the computing device 1404 may connect to the Internet using Wi-Fi or wireless access points, or the server may use a wireless network adapter to access the Internet. The computing device 1404 engages in two-way communication with any or all of the components and devices illustrated in FIG. 14, using the network 1402. Accordingly, the computing device 1404 may send data to and receive data from the remote computers 1406 over the network 1402.

Although illustrated as a single device, the remote computers 1406 may include multiple computing devices. In an aspect having a distributed network, the remote computers 1406 may be located at one or more different geographic locations. In an aspect where the remote computers 1406 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some aspects, the remote computers 1406 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other aspects, the remote computers 1406 may be physically located in a non-medical setting, such as a packing and shipping facility or deployed within a fleet of delivery or courier vehicles.

Continuing, the computing environment 1400 includes a data store 1408. Although shown as a single component, the data store 1408 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 1408 includes physical memory that is configured to store information encoded in data. For example, the data store 1408 may provide storage for computer-readable instructions, computer-executable instructions, data structures, data arrays, computer programs, applications, and other data that supports the functions and action to be undertaken using the computing environment 1400 and components shown in exemplary FIG. 14.

In a computing environment having distributed components that are communicatively coupled via the network 1402, program modules may be located in local and/or remote computer storage media including, for example only, memory storage devices. Aspects of the present invention may be described in the context of computer-executable instructions, such as program modules, being executed by a computing device. Program modules may include, but are not limited to, routines, programs, objects, components, and data structures that perform particular tasks or implement particular abstract data types. In aspects, the computing device 1404 may access, retrieve, communicate, receive, and update information stored in the data store 1408, including program modules. Accordingly, the computing device 1404 may execute, using a processor, computer instructions stored in the data store 1408 in order to perform aspects described herein.

Although internal components of the devices in FIG. 14, such as the computing device 1404, are not illustrated, those of ordinary skill in the art will appreciate that internal components and their interconnection are present in the devices of FIG. 14. Accordingly, additional details concerning the internal construction device are not further disclosed herein.

The present invention has been described in relation to particular aspects, which are intended in all respects to be illustrative rather than restrictive. Further, the present invention is not limited to these aspects, but variations and modifications may be made without departing from the scope of the present invention.

What is claimed is:

1. One or more non-transitory media having instructions that, when executed by one or more processors, cause the one or more processors to facilitate a plurality of operations, the operations comprising:

generating a combined vector, associated with healthcare information, based on a first set of historical text data and based further on a second set of historical contextual data, the first set of historical text data differing from the second set of historical contextual data;
generating a plurality of clusters based on an electronic machine-learning clustering model using the combined vector as input, wherein:
  (a) the electronic machine-learning clustering model is trained based on data associated with instances of first information selected from a group comprising the first set of historical text data and the second set of historical contextual data, and
  (b) the plurality of clusters includes the first set of historical text data and further include the second set of historical contextual data;
identifying a primary cluster in the plurality of clusters that is a best match to the combined vector;
performing natural language processing on second information associated with the primary cluster;
based at least on the natural language processing:
  assigning a relevance score, for at least a portion of a plurality of text blocks in the primary cluster, corresponding to a respective relevance of at least a portion of the plurality of text blocks to information associated with at least a portion of the combined vector;
identifying a primary text block in the plurality of text blocks of the primary cluster having a highest relevance score; and
in response to the identifying of the primary text block in the plurality of text blocks of the primary cluster having the highest relevance score:
  communicating the primary text block for display as a recommended selection for automatic population into at least a narrative field, of a healthcare related electronic document, configured to receive free-form narrative text.

2. The one or more non-transitory media of claim 1, wherein generating the combined vector comprises:
identifying categorical data in one or more of the first set of historical text data or the second set of historical contextual data, wherein the categorical data is incompatible for input to the electronic machine-learning clustering model; and
transforming the categorical data into dummy variables, wherein the dummy variables are used to generate the combined vector.

3. The one or more non-transitory media of claim 1, wherein the operations further comprise reducing data sparsity of the combined vector by:
applying Principle Component Analysis (PCA) to the combined vector to identify sparse columns of the combined vector, wherein the combined vector has n dimensions, one dimension for each of a plurality of features; and
projecting the combined vector having n dimensions to a k dimensional vector space to reduce a total quantity of the sparse columns, wherein k<n.

4. The one or more non-transitory media of claim 1, wherein the electronic machine-learning clustering model includes a Density-Based Spatial Clustering of Applications with Noise (DBSCAN).

5. The one or more non-transitory media of claim 1, wherein when generating the plurality of clusters, a total quantity of the plurality of clusters is determined by one or more characteristics of the first set of text data and the second set of historical contextual data in the combined vector, wherein a plurality of cluster tags are attached to the combined vector, and wherein the plurality of cluster tags map features of the first set of text data and the second set of historical contextual data to one or more of the plurality of clusters.

6. The one or more non-transitory media of claim 1, wherein the plurality of clusters includes one or more portions of physician-specific patient-encounter data or patient-specific context data.

7. The one or more non-transitory media of claim 6, wherein the primary cluster is identified, subsequent to reducing a data sparsity, by:
identifying one cluster in the plurality of clusters that corresponds to a set of text blocks in one or more of the physician-specific patient-encounter data or the patient-specific context data, wherein the set of text blocks in the one cluster have a greatest similarity to the combined vector relative to other clusters in the plurality of clusters; and
designating the one cluster as the primary cluster based on the one cluster have the greatest similarity to the combined vector relative.

8. The one or more non-transitory media of claim 1, wherein the primary text block includes text selected from a group comprising unstructured text, text other than a medical or billing code, and text other than a medical concept.

9. The one or more non-transitory media of claim 1, wherein the narrative field is configured to receive narrative text from a clinician describing a patient encounter, and wherein the primary text block includes unstructured text.

10. The one or more non-transitory media of claim 1, wherein the primary text block comprises a narrative note.

11. The one or more non-transitory media of claim 1, wherein the primary text block includes a narrative note describing a patient encounter.

12. The one or more non-transitory media of claim 1, wherein the primary text block includes a narrative note created by a clinician and describing a patient encounter.

13. The one or more non-transitory media of claim 1, wherein the primary text block includes content other than a medical code, billing code, or medical concept.

14. The one or more non-transitory media of claim 1, wherein the primary text block includes content other than a medical concept.

15. The one or more non-transitory media of claim 1, wherein the primary text block includes first text of a first type and second text of a second type, wherein the first type excludes structured text, medical and billing codes, and medical concepts, and wherein the second type includes content selected from a group comprising structured text, a medical or billing code, and a medical concept.

16. The one or more non-transitory media of claim 1, wherein the primary text block includes first text of a first type and second text of a second type, wherein the first type excludes structured text, and wherein the second type includes structured text.

17. The one or more non-transitory media of claim 1, wherein generating the combined vector comprises generating a physician-specific vector from the first set of historical text data and a patient-specific vector from the second set of historical contextual data.

18. The one or more non-transitory media of claim 17, wherein the combined vector is generated based on the physician-specific vector and the patient-specific vector.

19. The one or more non-transitory media of claim 1, wherein the primary text block includes a narrative input by a clinician documenting reasons and details regarding a clinical encounter with a patient, including a medical history of the patient and a chief complaint of the patient.

20. The one or more non-transitory media of claim 1, wherein the primary text block includes first text of a first type and second text of a second type, wherein the first type excludes structured text, medical and billing codes, and medical concepts, and wherein the second type includes a structured text element, a medical or billing code, and a medical concept.

21. The one or more non-transitory media of claim 1, wherein the primary text block includes first text of a first type and second text of a second type, wherein the first type excludes structured text, medical and billing codes, and medical concepts, and wherein the second type includes a medical concept.

22. The one or more non-transitory media of claim 1, wherein the primary text block includes a plurality of elements selected from a group comprising: a clinical fact, a clinical observation, and a contextual data item.

23. The one or more non-transitory media of claim 1, wherein the primary text block includes a medical assessment describing a patient encounter.

24. The one or more non-transitory media of claim 1, wherein the operations further comprise decreasing a dimensionality of the combined vector prior to inputting the combined vector to the electronic machine-learning clustering model to generate the plurality of clusters.

25. The one or more non-transitory media of claim 1, wherein the operations further comprise communicating the primary text block for display as a recommended selection for automatic population of a text assessment field of an electronic document.

26. The one or more non-transitory media of claim 1, wherein the primary text block includes a plurality of clinical assessments, and wherein the primary text block is communicated for display as a recommended selection for automatic population of a text narrative field of an electronic document.

27. The one or more non-transitory media of claim 1, wherein the operations further comprise:
retraining the electronic machine-learning clustering model based on additional data associated with the instances; and
reinputting to the retrained electronic machine-learning clustering model information associated with an additional combined vector to generate an additional plurality of clusters.

28. A system having one or more processors configured to facilitate a plurality of operations, the operations comprising:
generating a combined vector, associated with healthcare information, based on a first set of historical text data and based further on a second set of historical contextual data, the first set of historical text data differing from the second set of historical contextual data;
generating a plurality of clusters based on an electronic machine-learning clustering model using the combined vector as input, wherein:
(a) the electronic machine-learning clustering model is trained based on data associated with instances of first information selected from a group comprising the first set of historical text data and the second set of historical contextual data, and
(b) the plurality of clusters includes the first set of historical text data and further include the second set of historical contextual data;
identifying a primary cluster in the plurality of clusters that is a best match to the combined vector;
performing natural language processing on second information associated with the primary cluster;
based at least on the natural language processing:
assigning a relevance score, for at least a portion of a plurality of text blocks in the primary cluster, corresponding to a respective relevance of at least a portion of the plurality of text blocks to information associated with at least a portion of the combined vector;
identifying a primary text block in the plurality of text blocks of the primary cluster having a highest relevance score; and
in response to the identifying of the primary text block in the plurality of text blocks of the primary cluster having the highest relevance score:
communicating the primary text block for display as a recommended selection for automatic population into at least a narrative field, of a healthcare related electronic document, configured to receive free-form narrative text.

29. The system of claim 28, wherein generating the combined vector comprises:
identifying categorical data in one or more of the first set of historical text data or the second set of historical contextual data, wherein the categorical data is incompatible for input to the electronic machine-learning clustering model; and
transforming the categorical data into dummy variables, wherein the dummy variables are used to generate the combined vector.

30. The system of claim 28, wherein the operations further comprise reducing data sparsity of the combined vector by:
applying Principle Component Analysis (PCA) to the combined vector to identify sparse columns of the combined vector, wherein the combined vector has n dimensions, one dimension for each of a plurality of features; and
projecting the combined vector having n dimensions to a k dimensional vector space to reduce a total quantity of the sparse columns, wherein k<n.

31. The system of claim 28, wherein the electronic machine-learning clustering model includes a Density-Based Spatial Clustering of Applications with Noise (DBSCAN).

32. The system of claim 28, wherein when generating the plurality of clusters, a total quantity of the plurality of clusters is determined by one or more characteristics of the first set of text data and the second set of historical data in the combined vector, wherein a plurality of cluster tags are attached to the combined vector, and wherein the plurality of cluster tags map features of the first set of text data and the second set of historical contextual data to one or more of the plurality of clusters.

33. The system of claim 28, wherein the primary cluster is identified, subsequent to reducing a data sparsity, by:
identifying one cluster in the plurality of clusters that corresponds to a set of text blocks in one or more of physician-specific patient-encounter data or patient-specific context data, wherein the set of text blocks in the one cluster have a greatest similarity to the combined vector relative to other clusters in the plurality of clusters; and
designating the one cluster as the primary cluster based on the one cluster have the greatest similarity to the combined vector relative.

34. A method, comprising:
generating a combined vector, associated with healthcare information, based on a first set of historical text data and based further on a second set of historical contextual data, the first set of historical text data differing from the second set of historical contextual data;
generating a plurality of clusters based on an electronic machine-learning clustering model using the combined vector as input, wherein:
  (a) the electronic machine-learning clustering model is trained based on data associated with instances of first information selected from a group comprising the first set of historical text data and the second set of historical contextual data, and
  (b) the plurality of clusters includes the first set of historical text data and further include the second set of historical contextual data;
identifying a primary cluster in the plurality of clusters that is a best match to the combined vector;
performing natural language processing on second information associated with the primary cluster;
based at least on the natural language processing:
  assigning a relevance score, for at least a portion of a plurality of text blocks in the primary cluster, corresponding to a respective relevance of at least a portion of the plurality of text blocks to information associated with at least a portion of the combined vector;
identifying a primary text block in the plurality of text blocks of the primary cluster having a highest relevance score; and
in response to the identifying of the primary text block in the plurality of text blocks of the primary cluster having the highest relevance score:
  communicating the primary text block for display as a recommended selection for automatic population into at least a narrative field, of a healthcare related electronic document, configured to receive free-form narrative text.

35. The method of claim 34, further comprising: reducing a data sparsity of the combined vector prior to generating the plurality of clusters using the combined vector as input to the electronic machine-learning clustering model.

36. The method of claim 35, further comprising receiving a user input that includes a selection of the primary text block for automatic population of the healthcare related electronic document, communicating a value of one to a rule engine as feedback for subsequent cluster identifications.

37. The method of claim 34, further comprising receiving user input that does not select the primary text block.

38. The method of claim 37, wherein when the user input does not select the primary text block for automatic population of the electronic healthcare related document, communicating a value of zero to a rule engine, as feedback for subsequent cluster identifications.

39. The method of claim 34, further comprising:
combining the first set of historical text data and the second set of historical contextual data to generate the combined vector, wherein:
  (a) the first set of historical text data is stored at a first database of clinician notes, and
  (b) the second set of historical contextual data is stored at a second database of patient demographic information.

40. The method of claim 34, further comprising receiving user input that includes an edited version of the primary text block, wherein when the user input includes a selection of the edited version of the primary text block for automatic population of the healthcare related electronic document, communicating the edited version of the primary text block to a machine learning engine, wherein the edited version is stored as new historical data.

* * * * *